United States Patent
Zhao et al.

(10) Patent No.: US 6,720,420 B2
(45) Date of Patent: *Apr. 13, 2004

(54) PHOTOCHROMIC OXAZINE COMPOUNDS AND METHODS FOR THEIR MANUFACTURE

(75) Inventors: Weili Zhao, Zurich (CH); Erick M. Carreira, Zumikon (CH)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/029,579

(22) Filed: Dec. 21, 2001

(65) Prior Publication Data

US 2003/0149032 A1 Aug. 7, 2003

(51) Int. Cl.$^7$ .............................................. C07D 498/00

(52) U.S. Cl. .............................. 544/99; 544/70; 544/71; 546/64

(58) Field of Search .............................. 546/64; 544/70, 544/71, 99

(56) References Cited

FOREIGN PATENT DOCUMENTS

| DD | 153 690 A | 1/1982 |
|---|---|---|
| DD | 156 372 A | 8/1982 |

*Primary Examiner*—Amelia Owens

(57) ABSTRACT

The present invention provides oxazine compounds having aromatic, heteroaromatic, or aliphatic substituents at the 2 position of the oxazine moiety. Additionally, a one pot method with excellent yields is provided for producing the compounds

10 Claims, No Drawings

PHOTOCHROMIC OXAZINE COMPOUNDS AND METHODS FOR THEIR MANUFACTURE

FIELD OF THE INVENTION

The present invention relates to oxazine compounds. In particular, the invention provides oxazine compounds and methods for their manufacture, which compounds are useful as photochromic compounds.

BACKGROUND OF THE INVENTION

Various classes of photochromic compounds have been synthesized and suggested for use in applications in which reversible color changes or darkening is induced by sunlight. For example, spirooxazine and chromene compounds are known for excellent fatigue resistance. Additionally, photochromic 2,2-disubstituted [2H-1,4]-naphthoxazine compounds, such as those are disclosed in U.S. Pat. No. 5,801,243, are known. These compounds have better fatigue resistance than chromene compounds, but are disadvantageous in that methods for their preparation are extremely limited. Thus, a need exists for additional photochromic oxazine compounds that overcome the disadvantages of the known compounds.

DESCRIPTION OF THE INVENTION AND ITS PREFERRED EMBODIMENTS

The present invention provides oxazine compounds having aromatic, heteroaromatic, or aliphatic substituents at the 2 position of the oxazine moiety. Additionally, a one pot method with excellent yields is provided for producing the compounds.

In one embodiment, the invention provides a compound comprising the formula:

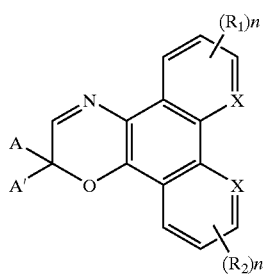

I wherein X is nitrogen or carbon;
$R_1$ and $R_2$ are each independently hydrogen, hydroxy, nitro, cyano, allyl, a linear or branched $(C_1-C_{20})$alkyl, $(C_3-C_{20})$cycloalkyl, $(C_1-C_{20})$alkoxy, $(C_1-C_{20})$alkylacetylenyl, phenylacetylenyl, $(C_1-C_{20})$alkenyl, phenylvinyl, a halogen, a halo$(C_1-C_{20})$alkyl, halo$(C_3-C_{20})$cycloalkyl, halo$(C_1-C_{20})$alkoxy, substituted with at least one halogen atom wherein the halogen is fluoro, chloro, bromo, or iodo, unsubstituted aryl, aryl substituted with $(C_1-C_6)$alkyl or $(C_1-C_6)$alkoxy or aryloxy, and preferably phenyl or naphthyl, unsubstituted heteroaryl or heteroaryl substituted with $(C_1-C_6)$alkyl or $(C_1-C_6)$alkoxy and preferably furyl, thienyl, pyrryl, indolyl, or pyridyl, arylalkyl or arylalkyl or heteroarylalkyl substituted with $(C_1-C_6)$alkyl or $(C_1-C_6)$alkoxy, substituted or unsubstituted nitrogen-containing heterocyclic ring, —N($R_1$)$R_2$ or CON($R_1$)$R_2$ wherein $R_1$ and $R_2$ are each independently hydrogen, $(C_1-C_{20})$alkyl, $(C_3-C_{20})$cycloalkyl, unsubstituted phenyl or phenyl substituted with $(C_1-C_6)$alkyl or $(C_1-C_6)$alkoxy, or a —OCOR or —COOR or —COR group wherein R is hydrogen, $(C_1-C_{20})$alkyl, $(C_3-C_{20})$cycloalkyl, or substituted or unsubstituted aryl or heteroaryl;
n is an integer from 0 to 4; and
A and A' are each independently:
(a) a linear or branched $(C_1-C_{12})$alkyl, $(C_3-C_{12})$cycloalkyl, aryl$(C_1-C_6)$alkyl, heteroaryl$(C_1-C_6)$alkyl, $(C_1-C_6)$alkoxy$(C_1-C_6)$alkyl, $(C_1-C_{12})$alkoxy, halo$(C_1-C_{12})$alkyl, $(C_1-C_{12})$haloalkoxy, or $(C_1-C_{12})$alkylthio wherein each of the aryl preferably are phenyl or naphthyl and each of the heteroaryl may be furyl, thienyl, pyrryl, indolyl, benzofuryl, benzothienyl, pyridyl, dibenzofuryl, dibenzothienyl, or carbazolyl;
(b) unsubstituted or mono- di- or tri-substituted aryl groups, such as phenyl and naphthyl;
(c) unsubstituted or mono-, or di-substituted heteroaromatic groups, such as furyl, thienyl, pyrryl, indolyl, benzofuryl, benzothienyl, pyridyl, dibenzofuryl, dibenzothienyl, carbazolyl;
(d) a group of either of the formulae:

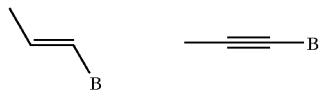

wherein B is hydrogen, $(C_1-C_{12})$alkyl, unsubstituted or mono- or di-substituted aryl, such as phenyl and naphthyl
wherein each of said aryl and heteroaromatic substituents in (b), (c) and (d) are nitro, amino, cyano, hydroxy, epoxy, vinyl, allyl, hydroxyethoxy, methoxyethoxy, hydroxyethoxyethoxy, methoxyethoxy
fluoro, chloro, bromo, or iodo, $(C_1-C_{12})$alkyl, $(C_1-C_{12})$alkoxy, $(C_1-C_{12})$alkylaryl, aryl, aryloxy, aryl$(C_1-C_{12})$alkyl, aryl$(C_1-C_{12})$alkoxy, $(C_1-C_{12})$alkoxyaryl, halo$(C_1-C_{12})$alkyl, haloaryl, cyclo$(C_3-C_{12})$alkyl; cyclo$(C_1-C_{12})$alkoxy, aryloxyaryl, aryloxy$(C_1-C_{12})$alkyl, aryloxy$(C_1-C_{12})$alkoxy, acryloxy, methacryloxy, or
a heterocyclic nitrogen-containing substituent, including, without limitation, N-$(C_1-C_{12})$alkylpiperizino, N-aryl-piperizino, aziridino, indolino, pyrrolidino, pyrrolino, piperidino, $(C_1-C_4)$alkylpiperidino, di$(C_1-C_4)$alkylpiperidino, 4-piperidinopiperidino, morpholino, 2,6-di$(C_1-C_4)$alkylmorpholino, thiomorpholino, thioazolidino, tetrahydroquinolino, pyrryl, or —N($R_1$)$R_2$ or CON($R_1$)$R_2$ wherein $R_1$ and $R_2$ are each independently hydrogen, $(C_1-C_{12})$alkyl, $(C_3-C_{12})$cycloalkyl, phenyl, mono- or di-substituted phenyl, a —COR, —OCOR or —COOR group wherein R is hydrogen, $(C_1-C_{12})$alkyl, $(C_3-C_{12})$cycloalkyl, halo$(C_1-C_6)$alkyl, unsubstituted, mono- or di-substituted phenyl, or unsubstituted, mono- or di-substituted naphthyl, unsubstituted, mono- or di-substituted furyl or thienyl;
(e) unsubstituted or mono-substituted pyrazolyl, pyridyl, imidazolyl, pyrazolinyl, imidazolinyl, or acridinyl, wherein the substituents are each independently $(C_1-C_6)$alkyl, $(C_1-C_6)$alkoxy, fluoro, chloro, phenyl; or (f) a group represented by either of the formulae:

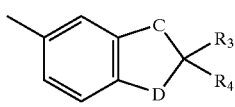 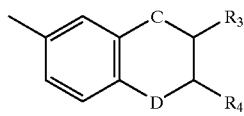

wherein C and D are each independently carbon, oxygen, $(C_1-C_{12})$alkyl nitrogen, or $(C_1-C_{12})$acyl nitrogen and $R_3$ and $R_4$ are each independently hydrogen or $(C_1-C_{12})$alkyl.

In embodiments in which halogen is selected, preferably it is fluoro, chloro or bromo.

In a preferred embodiment, X is carbon or nitrogen, $R_1$ and $R_2$ are each independently hydrogen, nitro, cyano, allyl, fluoro, chloro, bromo, trifluoromethyl, trichloromethyl, pyrrolidino, piperidino, morpholino, phenyl, benzyl, a linear or branched $(C_1-C_6)$alkyl, $(C_1-C_6)$alkoxy, or a —OCOR or —COOR group wherein R is hydrogen, $(C_1-C_6)$alkyl, or $(C_3-C_6)$cycloalkyl;

n is an integer from 0 to 2; and

A and A' are each independently:
(a) a linear or branched $(C_1-C_6)$alkyl, $(C_3-C_6)$ cycloalkyl; aryl$(C_1-C_4)$alkyl heteroaryl$(C_1-C_4)$ alkyl, or $(C_1-C_6)$alkoxy$(C_1-C_6)$alkyl;
(b) unsubstituted or mono- or di-substituted aryl, such as phenyl or naphthyl, preferably substituted in either or both the meta or para positions;
(c) unsubstituted or mono-substituted heteroaromatic groups, such as furyl, thienyl, pyrryl, indolyl, benzofuryl, benzothienyl, pyridyl, dibenzofuryl, dibenzothienyl, or carbazolyl;

wherein each of the aryl and heteroaromatic substituents in (b) and (c) are independently nitro, amino, cyano, hydroxy, epoxy, hydroxyethoxy, methoxyethoxy, hydroxyethoxyethoxy, methoxyethoxyethoxy, fluoro, chloro, bromo, or iodo, vinyl, allyl, trifluoromethyl, phenyl, $(C_1-C_6)$alkyl, $(C_1-C_6)$alkoxy, cyclo$(C_3-C_6)$alkyl, cyclo $(C_1-C_6)$alkoxy, $(C_1-C_6))$alkylamino, di$(C_1-C_6)$alkylamino, diarylamino, phenylacetylenyl, phenylvinyl, a heterocyclic nitrogen-containing substituent, including, without limitation, N$(C_1-C_6)$alkylpiperazino, N-aryl-piperizino, aziridino, indolino, pyrrolidino, pyrrolino, piperidino, $(C_1-C_4)$alkylpiperidino, di$(C_1-C_4)$alkylpiperidino, 4-piperidinopiperidino, morpholino, 2,6-di$(C_1-C_4)$ alkylmorpholino, thiomorpholino, thioazolidino, tetrahydroquinolino, pyrryl, or a —N$(R_1)R_2$, CON$(R_1)R_2$ wherein $R_1$ and $R_2$ are each independently hydrogen, $(C_1-C_6)$alkyl, $(C_3-C_6)$cycloalkyl, phenyl, or —COR, —OCOR or —COOR wherein R is hydrogen, $(C_1-C_6)$alkyl, $(C_3-C_6)$cycloalkyl, or phenyl.

More preferably, X carbon or nitrogen; $R_1$, $R_2$ are each independently hydrogen, nitro, cyano, fluoro, chloro, bromo, pyrrolidino, piperidino, morpholino, phenyl, benzyl, $(C_1-C_4)$alkyl, or $(C_1-C_4)$alkoxy;

n is an integer from 0 to 2; and

A and A' are each independently a linear or branched $(C_1-C_4)$alkyl, $(C_3-C_6)$cycloalkyl, unsubstituted or mono-, or di-substituted phenyl, preferably substituted in either or both the meta and para positions with a substituent selected from the group consisting of nitro, amino, acyl, cyano, methoxy, ethoxy, methoxyethoxy, fluoro, chloro, vinyl, allyl, methoxycarbonyl, ethoxycarbonyl, $(C_1-C_4)$alkyl, di$(C_1-C_4)$alkylamino, piperazino, piperidino, arylperidino, morpholino, pyrrolidino, aziridino, acryloxy, methacryloxy, phenylacetylenyl, and phenylvinyl;

Unsubstituted or mono-substituted heteroaromatic groups, such as furyl, thienyl, and pyrryl subsituted with a substituent selected from the group consisting of $(C_1-C_4)$alkyl, and phenyl.

Most preferably, the inventions provides a compound selected from the group consisting of:

2,2-diphenyl-phenanthro (9,10)-2H-[1,4]-oxazine,
2-(p-methoxyphenyl)-2-phenyl-phenanthro (9,10)-2H-[1,4]-oxazine,
2-(p-fluorophenyl)-2-(p-methoxyphenyl)-phenanthro (9,10)-2H-[1,4]-oxazine,
2,2-Bis(p-methoxyphenyl)-phenanthro (9,10)-2H-[1,4]-oxazine,
2-(p-methoxyphenyl)-2-(p-morpholinophenyl)-phenanthro (9,10)-2H-[1,4]-oxazine,
2-(p-methoxyphenyl)-2-(p-piperidinophenyl)-phenanthro (9,10)-2H-[1,4]-oxazine,
2-methyl-2-phenyl-phenanthro (9,10)-2H-[1,4]-oxazine,
2-cyclopropyl-2-phenyl-phenanthro (9,10)-2H-[4]-oxazine,
2,2-diphenyl-6,11-dinitro-phenanthro (9,10)-2H-[1,4]-oxazine,
2-(p-methoxyphenyl)-2-phenyl-6,11-dinitro-phenanthro (9,10)-2H-[1,4]-oxazine,
2,2-Bis(p-methoxyphenyl)-6,11-dinitro-phenanthro (9,10)-2H-[1,4]-oxazine,
2,2-diphenyl-phenanthrolino (5,6)-2H-[1,4]-oxazine,
2-(p-methoxyphenyl)-2-phenyl-phenanthrolino (5,6)-2H-[1,4]-oxazine and
2,2-Bis(p-methoxyphenyl)-phenanthrolino (5,6)-2H-[1,4]-oxazine.

A mild synthetic methodology for preparing the oxazine compound of Formula I is shown below as Reaction A, wherein a disubstituted acrylic acid, a quinone, an azide source such as sodium azide, lithium azide, diphenylphosphoryl azide ("DPPA"), or trimethylsilylazide ("TMSA"), an organic base including, without limitation, triethylamine, diisopropyl amine, diisopropyl ethylamine, pyridine, piperidine, morpholine, N-alkyl morpholine, 1,8-diazobicyclo[5,4,0]undec-7-ene ("DBU"), and a trisubstituted arsen oxide such as triphenyl arsen oxide may be used as reacting agents. The disubstituted acrylic acid may be used to undergo a series of transformations to form aza-ylide intermediate, which may react with a quinone such as phenanthrene (9,10)-dione, phenanthroline(5,6)-dione, to form the desired photochromic oxazine Reaction A

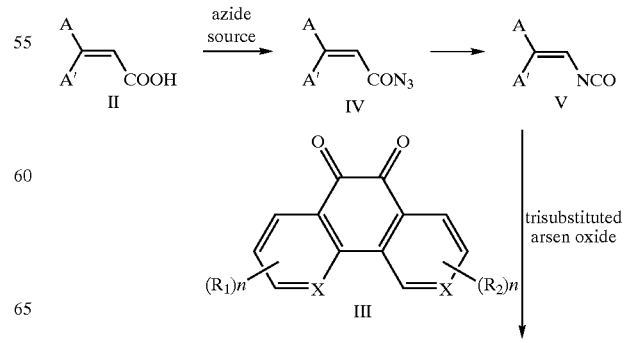

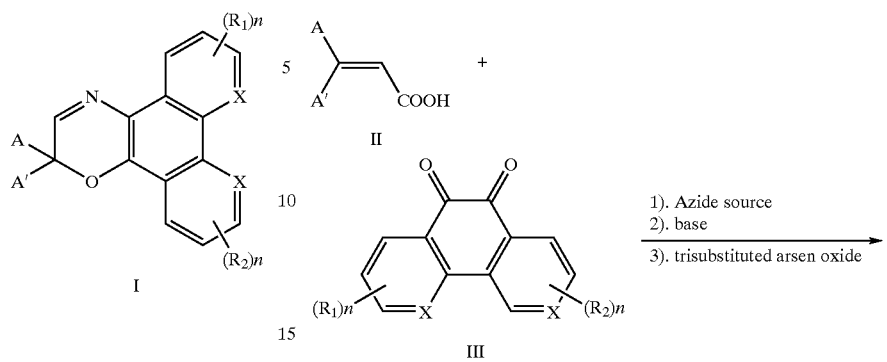

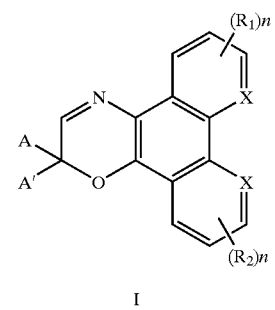

The key intermediate of the reaction is a highly reactive isocyanate derivative. The isocyanate may be in situ generated from substituted acrylic azide which in turn may be formed in situ from substituted acrylic acid. The isocyanate is converted to aza-ylide in the presence of catalytic amount of tri-substituted arsen oxide including, without limitation, triphenyl arsen oxide. The arsen ylide reacts immediately with quinone derivative to form the desired oxazine compound and regenerated triphenyl arsen oxide. The generation of the isocyanate from acrylic acid may be conducted by rearrangement of carboxylic azide derivative generated from acid using various reagent combinations under various conditions known in the art including, without limitation, acyl chloride-sodium azide, chloroformate-sodium azide, DPPA, TMSA, in the presence of organic base inclduing, without limitation, triethylamine, diisopropyl amine, diisopropyl ethylamine, pyridine, piperidine, morpholine, N-alkyl morpholine, DBU, and the like. DPPA and TMSA, methyl chloroformate-sodium azide, and methyl chloroformate-lithium azide are preferred azide sources.

One advantage of the above-described methodology is that all of the intermediates may be generated in situ, without purification. The reaction may be conducted either step-wise or, preferably, as a one-pot reaction. In the step-wise reaction, as shown in Reaction A, di-substituted acrylic acid is transformed into di-substituted acrylic acid chloride by treatment with acyl chloride such as thionyl chloride, acetyl chloride, or oxalyl chloride. The acrylic acid chloride is then treated with sodium azide or lithium azide to generate substituted acyl azide, or may be reacted with chloroformate such as methyl chloroformate in the presence of organic base to form mixed anhydride, then treated with sodium azide or lithium azide to generated substituted acyl azide.

Alternatively, substituted acrylic azide may be obtained by reaction with DPPA or TMSA in the presence of organic base. The organic base may be a secondary or tertiary amine including, without limitation, triethylamine, diisopropyl amine, diisopropyl ethylamine, pyridine, piperidine, morpholine, N-alkyl morpholine, DBU, and the like. Upon heating, a arrangement of acyl azide occurs to form the isocyanate derivative of the compound of Formula III. The isocyanate derivative may be reacted with quinone such as phenanthrene(9,10)-dione or phenanthroline(5,6)-dione in the presence of catalytic amount of trisubstituted arsen oxide such as triphenyl arsen oxide to form the desired photochromic oxazine.

The oxazine compounds may be obtained by more efficient, high yielding, one-pot methodology shown as Reaction B.

In this method, the reaction may be conducted simply by mixing a substituted acrylic acid, an azide source, preferably DPPA or TMS azide, a mild organic base, such as triethylamine, diisopropyl amine, diisopropyl ethylamine, pyridine, piperidine, morpholine, N-alkyl morpholine, DBU, a quinone such as phenanthrene (9,10)-dione, phenanthroline(5,6)-dione, and a catalytic amount of triaryl arsen oxide such as triphenyl arsen oxide, in a suitable organic solvent under heating for a time sufficient to complete the reaction, usually between about 1 and about 15 hours.

Reactive effective amounts of the mixture constituents are used meaning an amount suitable to produce the desired oxazine compound. The amount of trisubstituted arsen oxide may be about 1 mol percent to 20 mol percent, preferably about 2 to 10 mol percent, more preferably about 5 mol percent. The azide source such as DPPA and TMS azide is preferably used in about 1 to 5 equivalents compared with the di-substituted acrylic acid. The amount of organic base used may be about 1 to about 100 equivalents, preferably about 1 to 10 equivalents, more preferably about 2 to about 6 equivalents. Quinone such as phenanthrene (9,10)-dione, phenanthroline(5,6)-dione, may be used in about 0.5 to 1.5 equivalents, preferably about 0.6 to 0.8 equivalents. The preferred ratio of acrylic acid:azide source:base:quinone:triaryl arsenoxide is about 1:1.2:5:0.7:0.05.

Useful organic solvents include, without limitation, benzene, dioxane, tetrahydofuran (THF), toluene, and xylene, and the like and mixtures thereof. Reaction temperatures will vary and typically range from about 40° C. to about 150° C. In a preferred embodiment, the solvent is nonpolar benzene or toluene and the reaction condition is carried out at about 50 to about 110° C. for about 1 to about 15 hours. More preferably, the solvent is toluene or benzene and the reaction is carried out at about 60 to about 80° C. for about 2 to 4 hours.

The substituted acrylic acid may be prepared by the either of two reactions, Reactions C and D, illustrated as follows.

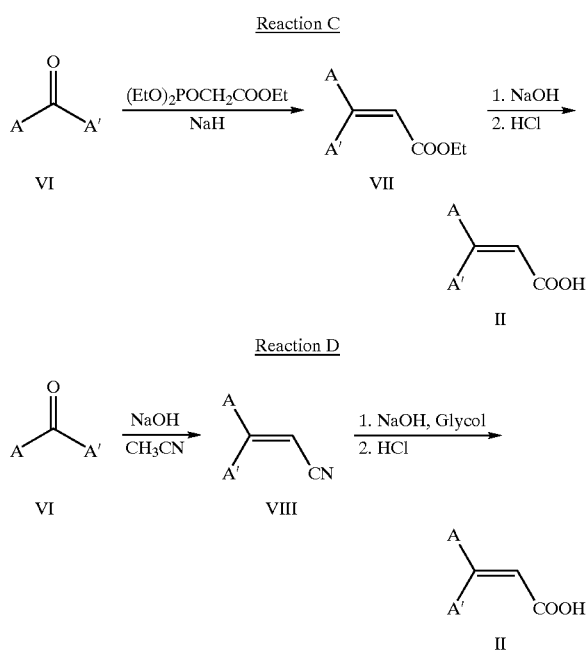

Reaction C, a Hornor-Emmons reaction as described in Tetrahedron, 52(31), 10455–10472 (1996), may be conducted starting from a ketone of Formula V. The resulting 3,3-disubstituted acrylic acid ethyl ester of Formula IV may be hydrolyzed to form disubstituted acrylic acid of Formula II. A, A' are the same as defined hereinabove.

In reaction D, a ketone is reacted with acetonitrile in the presence of an excess amount of a suitable base including, without limitation, sodium hydroxide to form the 2,2-disubstituted acrylonitrile of Formula V. This process is described in J. Org. Chem., 44(25), 4640–4649 (1979). After hydrolyzation with the base in a suitable organic solvent, followed by acidification, the disubstituted acrylic acid of Formula II may be obtained.

The oxazine compounds of the invention may be used singly, in combination, or in combination with other types of photochromic compounds, including without limitation naphthopyran and spirooxazines, or combinations thereof. The oxazines of the invention may be used in any applications in which organic photochromic substances are typically employed including, without limitation, ophthalmic lenses, windows, automotive transparencies, polymer films, and the like. The oxazines may be utilized in an organic solvent which solvent may be any suitable solvent including, without limitation, benzene, toluene, methyl ethylketone, acetone, ethanol, methanol, tetrahydrofuran, dioxane, ethyl acetate, ethylene glycol, xylene, cylcohexane, N-methyl pyrrolidinone, and the like and mixtures thereof.

Alternatively, the oxazines may be used in an organic polymer host by various means. For example, the oxazine may be dissolved or dispersed into the host material and polymerized with other components of the host material. Alternatively, the oxazine may be incorporated into a coating applied to one surface of the host material. As yet another alternative, the oxazine may be imbibed into or coated onto a surface of the host material.

Preferred host materials are optically clear plastics including, without limitation, polymers, copolymers, or a mixture of polymers. Exemplary host materials include, without limitation, poly(ally carbonate), polyepoxy, polyacrylates, polyethylene, polypropylene, polyvinyl chloride, polymethacrylates, poly (C$_1$–C$_{12}$)alkyl methacrylates, polyoxy(alkylene methacrylates, cellulose acetate, cellulose triacetate, cellulose acetate butyrate, acetyl cellulose, poly (vinyl acetate), poly (vinyl alcohol), polyurethanes, polythiourethane, polysiloxane, polyamide, polystyrene, and copolymers selected from the group consisting of acrylates, methacrylates, methyl methacrylates, ethylene glycol bis methacrylate, vinyl acetate, vinyl butyral, urethane, thiourethane, diethylene glycol bis (allylcarbonate), diethylene glycol dimethacrylate, diisopropenyl benzene, and the like.

The amount of oxazine used is an amount such that the organic host material to which the photochromic compound, or mixture of compounds, is applied or in which they are incorporated exhibits the desired resultant color. Typically, within limits, the more oxazine used, the greater the color intensity. Generally, about 0.001 to about 20% by weight of the polymer host is used.

Nonphotochromic dyes may be used in conjunction with the oxazines of the invention to adjust the tint. Additionally, antioxidants, UV absorbents, anti-radical agents and the like may also be used to improve photochromic properties.

In solution or in a polymer matrix, the oxazine compounds of the invention are colorless or pale yellow, and rapidly develop an intense coloration under UV irradiation. The oxazines will exhibit a wide range of color when activated by a source of ultraviolet radiation, from orange, reddish-orange, purple, to blue gray. A wide range of fading is also provided, the range being from one half hour to several seconds depending on the structure of the oxazine compound and solvent or matrix used.

One particular advantage of the oxazine compounds of the present invention is that the absorption spectra of the colored form of the activated oxazine typically shows two or three absorption bands covering a wide range in visible spectra. For example, 2-(p-methoxyphenyl)-2-(p-piperidinophenyl)-phenanthro (9,10)-2H-[1,4]-oxazine, upon activation in organic solution or in polymer exhibits a gray color that fades quickly. The compound's UV-visible spectra showed three bands covered the whole visible-region, which is ideal for application in sunglasses, spectacle lenses, and contact lenses.

The invention will be clarified further by consideration of the following, non-limiting examples.

EXAMPLES

Example 1

Step 1.

Into a 100 ml three-necked flask was charged solid KOH (3.30 g, 0.05 mole) and 25 ml acetonitrile under argon which was then heated to reflux. Benzophenone (9.1 g, 0.05 mole) in 20 ml acetonitrile was added in a stream with stirring. After 8 hours reflux, the hot reaction solution was poured onto 100 g crushed ice and extracted with dichloromethane (3×15 ml). The combined organic extract was washed with water, dried over anhydrous sodium sulfate, and filtered. Solvent was removed, the residue was purified by flash chromatography on silica gel (ether-hexane 1:5 as eluent), and 7.9 g of a colorless oil was obtained. Yield: 77%. $^1$HNMR showed the product to have a structure consistent with 3,3-diphenyl-acrylonitrile.

$^1$HNMR (CDCl$_3$): δ5.75 (s, 1H), 7.27–7.50 (m, 10H).

Step 2.

The 3,3-diphenyl-acrylonitrile (5.76 g, 2.81 mmol) produced in Step 1 and sodium hydroxide (11.2 g, 280 mmol) were refluxed in a mixture of 180 ml ethylene glycol and 1 ml water for 3 days. The reaction mixture was cooled and diluted with 100 ml water, acidified with 5 M hydrochloric acid until the pH was less than 1, filtered with suction and washed completely with water. The solid paste was dissolved in ethyl acetate, washed with dilute hydrochloric acid. The organic layer was separated and the aqueous layer was extracted twice with ethyl acetate. The combined ethyl acetate solution was dried over anhydrous sodium sulfate, and filtered. Solvent was removed in vacuo until the total volume was approximately 40 ml. The solution was filtered through a short silica gel column and washed with ethyl acetate. After removal of the solvent in vacuo, the residue was titrated with a small volume of hexane-ethyl acetate (4:1) and recrystallized from ethyl acetate/hexane. Colorless crystal (5.34 g) was obtained. Yield: 84.8%. $^1$HNMR showed the product to have a structure consistent with 3,3-diphenylacrylic acid.

$^1$HNMR (CDCl$_3$): δ 6.38 (s, 1H), 7.24–7.35 (m, 1H), 7.40–7.46 (m, 3H).

Step 3.

A mixture of the diphenylacrylic acid (225 mg, 1 mmol) of Step 2, DPPA (95%, 348 mg, 1.2 mmol), triethylamine (506 g, 5 mmol), phenanthrene-9,10-dione (146 mg, 0.7 mmol) and triphenyl arsen oxide (16 mg, 0.05 mmol) in dry toluene (12 ml) was heated to 60° C. over 3 hours. After chromatography (silica gel, dichloromethane-hexane 2:1 as eluent) and recrystallization from dichloromethane-hexane, 308 mg of 2,2-diphenyl-phenanthro (9,10)-2H-[1,4]-oxazine, was obtained as a colorless (slightly pale yellow) crystal. Yield: 100%.

$^1$HNMR (CDCl$_3$): δ 7.24–7.29 (m, 6H), 7.46–7.70 (m, 8H), 8.12 (s, 1H), 8.43–8.52 (m, 1H), 8.53–8.62 (m, 3H).

$^{13}$CNMR (CDCl$_3$): δ 79.5, 122.5, 122.7, 122.8, 123.0, 125.1, 126.9, 126.9, 127.1, 127.3, 127.6, 128.4, 128.6, 129.8, 131.3, 128.0, 141.4, 155.7.

Example 2

Step 1.

To a stirred suspension of sodium hydride (95%, 0.507 g, 20 mmol) in THF (15 ml) was added 2–3 ml a solution of triethylphosphono acetate (4.48 g, 20 mmol) in THF (20 ml). A tiny drop of ethanol was added to initialize the reaction, then the rest of the triethylphosphono acetate solution was added dropwise under ice-water cooling over 40 minutes. After 15 minutes of stirring, the reaction mixture was transferred into a dropping funnel and added dropwise to a boiling solution of 4-methoxybenzophenone (4.38 g, 20 mmol) in THF (20 ml). After 24 hours reflux, most of the solvent was removed. The cooled residue was added to a saturated solution of aqueous sodium chloride (20 ml) and extracted with dichloromethane. Removal of dichloromethane gave a pale yellow oil (5.42 g) which contained mainly (E) and (Z)-3-p-methoxyphenyl-3-phenyl-acrylic acid ethyl ester as characterized by $^1$HNMR and was used directly in the next step without further purification.

Step 2.

The oil obtained in Step 1 was hydrolyzed in a solution of KOH (5.07 g, methanol (30 ml) under reflux for 1 hour. The cooled reaction mixture was poured into ice-water, acidified with dilute hydrochloric acid until the pH was less than 1 and extracted with ethyl acetate (3×20 ml). The combined organic solution was dried over anhydrous sodium sulfate. Solvent was removed and the residue was recrystallized from ethyl acetate/hexane. A white solid was obtained. The mother liquid was subjected to chromatography and recrystallization. A total of 3.826 g desired product was obtained as white solid and 0.677 g unreacted ketone was recovered. Yield: 75.3%. $^1$HNMR showed that the recovered product to be a mixture of (E)- and (Z)-3-p-methoxyphenyl-3-phenyl-acrylic acid.

Step 3.

The procedure of Step 3 of Example 1 was repeated except that 3-p-methoxyphenyl-3-phenyl-acrylic acid (254.5 mg, 1 mmol) was used instead of 3,3-diphenyl-acrylic acid to obtain 290.7 mg of 2-(p-methoxyphenyl)-2-phenyl-phenanthro (9,10)-2H-[1,4]-oxazine, as pale yellow crystal. Yield: 100%.

$^1$HNMR (CDCl$_3$): δ 3.74 (s, 3H), 6.84 (d, 2H, J=8.7 Hz), 7.29–7.42 (m, 5H), 7.50–7.60 (m, 3H), 7.61–7.66 (m, 3H), 8.07 (s, 1H), 8.42–8.62 (m, 4H).

$^{13}$CNMR (CDCl$_3$): δ 55.2, 79.4, 114.0, 122.5, 122.7, 122.8, 122.8, 122.9, 125.1, 125.2, 126.8, 126.9, 127.0, 127.5, 128.3, 128.6, 129.8, 131.2, 133.3, 138.0, 141.6, 155.9, 159.7.

Example 3

Step 1.

A mixture of anisole (11.9 g, 0.11 mole) and p-fluorobenzoyl chloride (97%, 16.34 g, 0.1 mole) in dichloromethane (50 ml) was added aluminum chloride (14.67 g, 0.11 mole) in small portions with stirring under ice-water cooling. After addition, the reaction mixture was stirred at room temperature for 1 hour, poured into a mixture of crushed ice (400 g) and hydrochloric acid (20 ml), and stirred until the orange color discharged. The mixture was then extracted with dichloromethane, dried over sodium sulfate, passed through a short silica gel column and washed with dichloromethane. The solvent was removed, the residue was recrystallized from dichloromethane-hexane, and 21.96 g of a colorless crystal was obtained. Yield: 95.4%. $^1$HNMR showed the product to have a structure consistent with p-fluorophenyl-p-methoxyphenyl ketone.

$^1$HNMR (CDCl$_3$): δ 3.89 (s, 3H), 6.97 (d, 2H, J=8.7 Hz), 7.13 (dd, 2H, J=8.7 Hz), 7.76–7.84 (m, 4H).

Step 2.

The procedure of Step 2 of Example 2 was repeated except that p-fluorophenyl-p-methoxyphenyl ketone (4.60 g, 20 mmol) was used instead of p-methoxybenzophenone and the reaction time was 48 hours. The resulting oil contained mainly (E) and (Z)-3-p-fluorophenyl-3-p-methoxyphenyl acrylic acid ethyl ester, which was used in the next step without further purification.

Step 3.

The oil obtained in Step 2 was hydrolyzed in a mixture of KOH (5.2 g) and methanol (30 ml) for 80 minutes. The mixture was then cooled, solvent was removed in vacuo, and water (30 ml) was added. The mixture was filtered with suction, washed with water, and the filtrate extracted with ether (15 ml). The aqueous layer was separated and acidified with 4 M hydrochloric acid until the pH was less than 1. The solid was collected by filtration and recrystallized from dichloromethane/hexane, 4.8 g white crystal was obtained. Yield: 88.1%. $^1$HNMR showed the recovered product to have a structure consistent with a mixture of (E) and (Z) 3-p-fluorophenyl-p-methoxyphenyl-acrylic acid.

Step 4.

The procedure of Step 3 of Example 1 was repeated except that 3-p-fluorophenyl-p-methoxyphenyl-acrylic acid (272.3 mg, 1 mmol) was used instead of 3,3-diphenyl-acrylic acid to form the oxazine, 2-(p-fluorophenyl)-2-(p-methoxyphenyl)-phenanthro (9,10)-2H-[1,4]-oxazine, as a pale yellow crystal. Yield: 99.6%.

$^1$HNMR (CDCl$_3$): δ 3.74 (s, 3H), 6.85 (m, 2H), 7.04 (m, 2H), 7.38 (m, 2H), 7.46–7.60 (m, 3H), 7.62–7.70 (m, 3H), 8.02 (s, 1H), 8.43–8.47 (m, 1H), 8.54–8.63 (m, 3H).

$^{13}$CNMR (CDCl$_3$): δ 55.2, 79.0, 114.0, 115.3, 115.6, 115.6, 122.6, 122.7, 122.8, 125.0, 125.0, 125.1, 126.8, 127.3, 127.6, 128.4, 128.8, 128.9, 129.5, 131.1, 132.8, 137.2, 137.2, 137.7, 155.4, 159.6, 164.1.

Example 4
Step 1.

To a stirred suspension of sodium hydride (0.48 g, 20 mmol) in dry THF (20 ml) was added dropwise a solution of triethyl phosphonoacetate 4.48 g, 20 mmol) in dry THF (25 ml) under nitrogen with ice-water bath cooling. After 40 minutes, the solution was transferred to a dropping funnel, added dropwise to a refluxing solution of bis-(p-methoxyphenyl) ketone in dry THF (20 ml) over 20 minutes. The reaction mixture was refluxed for 48 hours and was then hydrolyzed with a saturated sodium chloride solution (40 ml). The aqueous phase was extracted with ether (3×70 ml). The combined organic extracts were dried, filtered and concentrated to afford a residue which was purified by chromatography eluting with methylenechloride/hexane (1:2). A colorless oil (4.23 g) was obtained. Yield: 67.8%. $^1$HNMR showed that the recovered product to have structure consistent with 3,3-bis(p-methoxyphenyl)-acrylic acid ethyl ester.

$^1$HNMR (CDCl$_3$): δ 1.16 (t, 3H, J=7.1 Hz), 3.81 (s, 3H), 3.84 (s, 3H), 4.07 (q, 2H, J=7.1 Hz), 6.22 (s, 1H), 6.84 (d, 2H, J=9.1 Hz), 6.90 (d, 2H, J=9.1 Hz), 7.15 (d, 2H, J=9.1 Hz), 7.24 (d, 2H, J=9.1 Hz).

Step 2.

The 3,3-bis(p-methoxyphenyl)-acrylic acid ethyl ester (4.23 g, 13.5 mmol) obtained in Step 1 was hydrolyzed in 22 ml methanol in the presence of KOH (3.7 g, 66 mmol) for 1 hour under reflux. The cooled reaction mixture was poured into ice-water (50 ml), acidified with dilute hydrochloric acid until the pH was less than 1. The resulting solid was filtered, washed with water, and recrystallized from ethylacetate/hexane. A white solid (3.6 g) was obtained. Yield: 93.78%. $^1$HNMR showed the recovered product to have a structure consistent with 3,3-bis(p-methoxyphenyl)-acrylic acid.

$^1$HNMR (CDCl$_3$): δ 3.82 (s, 3H), 3.85 (s, 3H), 6.22 (s, 1H), 6.85 (d, 2H, J=9.0 Hz), 6.91 (d, 2H, J=8.7 Hz), 7.17 (d, 2H, J=8.7 Hz), 7.24 (d, 2H, J=8.7 Hz).

Step 3.

The procedure of Step 3 of Example 1 was repeated except that 3,3-bis(p-methoxyphenyl)-acrylic acid (284.3 mg, 1 mmol) was used instead of 3,3-diphenyl-acrylic acid to form (2,2-Bis(p-methoxyphenyl)-phenanthro (9,10)-2H-[1,4]-oxazine, as a pale yellow crystal. Yield: 93.2%.

$^1$HNMR (CDCl$_3$): δ 3.75 (s, 6H), 6.85 (d, 2H, J=8.7 Hz), 7.41 (d, 2H, J=9.1 Hz), 7.52–7.60 (m, 1H), 7.62–7.68 (m, 3H), 8.03 (s, 1H), 8.43–8.47 (m, 1H), 8.54–8.63 (m, 3H).

$^{13}$CNMR (CDCl$_3$): δ 55.2, 79.3, 113.0, 122.5, 122.7, 122.8, 122.9, 125.1, 126.8, 127.3, 127.5, 128.5, 129.8, 131.2, 133.5, 156.1, 159.7.

Example 5
Step 1.

To a stirred suspension of sodium hydride (95%, 0.253 g, 10 mmol) in dioxane (20 ml) was added dropwise a solution of triethylphosphono acetate (2.31 g, 10 mmol) in dioxane (5 ml). After 20 minutes stirring, p-methoxyphenyl-p-morpholinophenyl ketone (2.28 g, 8 mmol) was added and refluxed for 45 hours, and most of the solvent was removed. Water was added to the cold residue and the mixture was extracted with ethyl acetate. Removal of solvent gave a pale, yellow oil which was used directly in the next step without further purification.

Step 2.

The oil obtained in Step 1 was hydrolyzed in a solution of KOH (2.0 g) in methanol (15 ml) under reflux for 1.5 hour. After removal of the solvent, the reaction mixture was added to ice-water, filtered with suction and washed with water. 0.4 g unreacted ketone was recovered. The filtrate was extracted with ether, the aqueous layer was separated and acidified with dilute hydrochloric acid, and extracted with dichloromethane (3×20 ml). The combined organic solution was dried over anhydrous sodium sulfate. The solvent was removed, the residue was recrystallized from ethyl dichloromethane/hexane and 1.72 g of a yellow crystal was obtained. $^1$HNMR showed that the recovered product to have structure consistent with a mixture of (E) and (Z)-3-p-methoxyphenyl-3-p-morpholinophenyl-acrylic acid.

Step 3.

The procedure of Step 3 of Example 1 was repeated except that 3-p-methoxyphenyl-3-p-morpholinophenyl-acrylic acid (339.4 mg, 1 mmol) was used instead of 3,3-diphenyl-acrylic acid to form 358 mg of 2-(p-methoxyphenyl)-2-(p-morpholinophenyl)-phenanthro (9,10)-2H-[1,4]-oxazine, as pale brown solid. Yield: 100%.

Example 6
Step 1.

To a stirred suspension of sodium hydride (95%, 0.253 g, 10 mmol) in THF (15 ml) was added dropwise a solution of triethylphosphono acetate (2.31 g, 10 mmol) in THF (5 ml). After 20 minutes stirring, p-methoxyphenyl-p-piperidinophenyl ketone (2.95 g, 10 mmol) was added and refluxed for 5 days, and most of the solvent was removed. The cooled residue was added water and extracted with ethyl acetate. Removal of the solvent gave a pale yellow oil which was used directly in the next step without further purification.

Step 2.

The oil obtained in Step 1 was hydrolyzed in a solution of KOH (2.8 g) in methanol (15 ml) under reflux for 1 hour. After removal of solvent, the reaction mixture was added to ice-water, filtered with suction and washed with water. 1.35 g unreacted ketone was recovered. The filtrate was extracted with ether, the aqueous layer was separated, acidified with dilute hydrochloric acid, and filtered with suction, and a 1.18 g of yellow solid was obtained. $^1$HNMR showed that the recovered product to have structure consistent with a mixture of (E) and (Z)-3-p-methoxyphenyl-3-p-piperidinophenyl-acrylic acid.

Step 3.

The procedure of Step 3 of Example 1 was repeated except that 3-p-methoxyphenyl-3-p-piperidinophenyl-acrylic acid (337.4 mg, 1 mmol) was used instead of 3,3-diphenyl-acrylic acid to form 336.8 mg of the desired photochromic oxazine, 2-(p-methoxyphenyl)-2-(p-piperidinophenyl)-phenanthro (9,10)-2H-[1,4]-oxazine, as a pale yellow solid. Yield: 96.5%.

Example 7
Step 1.

The procedure of Step 2 of Example 2 was repeated except that acetophenone (2.43 g, 20 mmol) was used instead of p-methoxybenzophenone and reaction time was 4 days. The resulting oil (3.78 g) was used in the next step without further purification.

Step 2.

The oil obtained in Step 2 was hydrolyzed in a mixture of potassium hydroxide (5.07 g) and methanol (30 ml) for 1 hour. The mixture was then cooled and the solvent was removed in vacuo. Water (30 ml) was added to the residue and extraction was carried out with ether ×2 (15 ml each). The aqueous layer was separated and acidified with 4 M hydrochloric acid until the pH was less than 1. The solid was collected by filtration and a 2.4 g white solid was obtained. Yield: 74%. $^1$HNMR showed the recovered product to have structure consistent with a mixture of (E) and (Z) 3-methyl-3-phenyl-acrylic acid.

Step 3.

The procedure of Step 3 of Example 1 was repeated except that 3-methy-3-phenyl-acrylic acid (272.3 mg, 1 mmol) was used instead of 3,3-diphenyl-acrylic acid, and phenanthrene-9,10-dione was used in amount of 191.2 mg, 0.9 mmol, and the reaction temperature was 80° C. to form 122 mg of the 2-methyl-2-phenyl-phenanthro (9,10)-2H-[1,4]-oxazine, as pale yellow crystal. Yield: 41.9%.

Example 8

Step 1.

The procedure of Step 1 of Example 7 was repeated except that cyclopropyl phenyl ketone (2.98 g, 20 mmol) was used instead of p-methoxybenzophenone and reaction time was 4 days. The resulting oil (4.42 g) was used in the next step without further purification.

Step 2.

The procedure of Step 2 of Example 7 was repeated except the oil (4.42 g) of Step 1 was used. 3.31 g of a white solid was obtained. Yield: 88%. $^1$HNMR showed the recovered product to have structures consistent with a mixture of (E) and (Z) 3-cyclopropyl-3-phenyl-acrylic acid.

Step 3.

The procedure of Step 3 of Example 1 was repeated except that 3-cyclopropyl-3-p-piperidinophenyl-acrylic acid (188 mg, 1 mmol) was used instead of 3,3-diphenyl-acrylic acid to form 195.5 mg of 2-cyclopropyl-2-(p-piperidinophenyl)-phenanthro (9,10)-2H-[1,4]-oxazine, as a pale yellow solid. Yield: 80%.

Example 9

The oxazine compounds of the Examples were dissolved in organic solvent, then exposed to UV irradiation at 365 nm for 15 seconds. The solutions developed an intense coloration and lost their color in the dark. The fading was expressed by the time that it took for one half of the optical density initially colored to disappear. The maximum absorptions in the visible region are given in the table below. The typical absorption spectra includes two bands: one below 470 nm and one above 490 nm. The relative intensity of the two band depends on the structure of the photochrome. The stronger the electron-donating ability of the substituents at the 2 position, the stronger the intensity of the absorption band at the longer wavelength.

What is claimed is:

1. A compound comprising the formula:

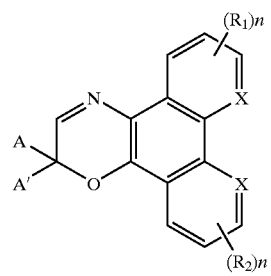

I wherein X is nitrogen or carbon;

$R_1$ and $R_2$ are each independently hydrogen, hydroxy, nitro, cyano, allyl, a linear or branched ($C_1$–$C_{20}$)alkyl, ($C_3$–$C_{20}$)cycloalkyl, ($C_1$–$C_{20}$)alkoxy, ($C_1$–$C_{20}$)alkylacetylenyl, phenylacetylenyl, ($C_1$–$C_{20}$)alkenyl, phenylvinyl, a halogen, a halo($C_1$–$C_{20}$)alkyl, halo($C_3$–$C_{20}$)cycloalkyl, halo($C_1$–$C_{20}$)alkoxy, substituted with at least one halogen atom wherein the halogen is fluoro, chloro, bromo, or iodo, unsubstituted aryl, ary; substituted with ($C_1$–$C_6$)alkyl or ($C_1$–$C_6$)alkoxy, or aryloxy, unsubstituted heteroaryl, heteroaryl substituted with ($C_1$–$C_4$)alkyl or ($C_1$–$C_6$)alkoxy, arylalkyl or substituted heteroarylalkyl, heteroarylakyl substituted with ($C_1$–$C_6$)alkyl or ($C_1$–$C_6$)alkoxy, substituted or unsubstituted nitrogen-containing heterocyclic ring, —N($R_1$)$R_2$ or CON($R_1$)$R_2$ wherein $R_1$ and $R_2$ are each independently hydrogen, ($C_1$–$C_{20}$)alkyl, ($C_3$–$C_{20}$)cycloalkyl, substituted phenyl, phenyl substituted with ($C_1$–$C_6$)alkyl or ($C_1$–$C_6$)alkoxy, or a —OCOR or —COOR or —COR group wherein R is hydrogen, ($C_1$–$C_{20}$)alkyl, ($C_3$–$C_{20}$)cycloalkyl, or substituted or unsubstituted aryl or heteroaryl;

n is an integer from 0 to 4; and

A and A' are each independently:
(a) a linear or branched ($C_1$–$C_{12}$)alkyl, ($C_3$–$C_{12}$)cycloalkyl, aryl($C_1$–$C_6$)alkyl, heteroaryl($C_1$–$C_6$)alkyl, ($C_1$–$C_6$)alkoxy($C_1$–$C_6$)alkyl, ($C_1$–$C_{12}$)alkoxy, halo($C_1$–$C_{12}$)alkyl, ($C_1$–$C_{12}$)haloalkoxy, or ($C_1$–$C_{12}$)alkylthio;
(b) unsubstituted or mono- di- or tri-substituted aryl groups wherein each of the substituents are nitro,

| Example | Hexane | toluene | Dioxane | Acetonitrile | Methanol |
|---|---|---|---|---|---|
| 1 | 660 s, 451 nm | 780 s, 456 nm | 858 s. 447 nm | 540 s, 444 nm | 528 s, 448 nm |
| 2 | 247 s, 474 nm | 247 s, 478 nm | 242 s, 469 nm | 154 s, 466 nm | 72 s, 471 nm |
| 3 | — | 269 s, 478 nm | 242 s, 478 nm | 154 s, 466 nm | 81.6 s, 470 nm |
| 4 | 88.8 s, 487 nm | 82.8 s, 493 nm | 74.4 s, 486 nm | 49.2 s, 483 nm | 20.4 s, 487 nm |
| 5 | 48 s, 510 nm | — | 28.5 s, 563 nm | 11.4 s, 569 nm | 3.6 s, 577 |
| 6 | 31.5 s, 559 nm | 20.4 s, 588 nm | 16 s, 581 nm | 4.9 s, 590 nm | — |
| 7 | 207 s, 430 nm | 190 s, | — | 110 s, 423 nm | 57.6 s, 438 nm |
| 8 | 81.6 s, 432 nm | 79.3 s, 436 nm | 86.6 s, 430 nm | 52.5 s, 427 nm | 26.6 s,395 nm | amino, cyano, hydroxy, epoxy, vinyl, allyl, hydroxyethoxy, methoxyethoxy, hydroxyethoxyethoxy, methoxyethoxyethoxy chloro, bromo, or iodo, $(C_1-C_{12})$alkyl, $(C_1-C_{12})$alkoxy, $(C_1-C_{12})$alkylaryl, aryl, aryloxy, aryl $(C_1-C_{12})$alkyl, aryl$(C_1-C_{12})$alkoxy, $(C_1-C_{12})$alkoxyaryl, halo$(C_1-C_{12})$alkyl, haloaryl, cyclo$(C_3-C_{12}$alkyl, cyclo$(C_1-C_{12})$alkoxy, aryloxyaryl, aryloxy$(C_1-C_{12})$alkyl, aryloxy$(C_1-C_{12})$alkoxy, acryloxy, methacryloxy, or
a heterocyclic nitrogen-containing substituent;
(c) unsubstituted or mono-, or di-substituted heteroaromatic groups;
(d) a group of either of the formulae:

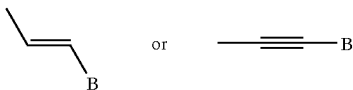

wherein B is hydrogen, $(C_1-C_{12})$alkyl, unsubstituted or mono- or di-substituted aryl;
(e) unsubstituted or mono-substituted pyrazolyl, pyridyl, imidazolyl, pyrazolinyl, imidazolinyl, or acridinyl, wherein the substituents are each independently $(C_1-C_6)$alkyl, $(C_1-C_6)$alkoxy, fluoro, chloro, phenyl; or
(f) a group represented by either of the formulae:

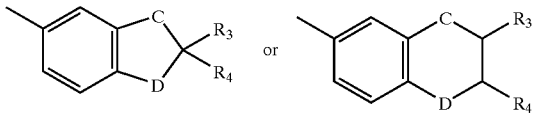

wherein C and D are each independently carbon, oxygen, $(C_1-C_{12})$alkyl nitrogen, or $(C_1-C_{12})$acyl nitrogen and $R_3$ and $R_4$ are each independently hydrogen or $(C_1-C_{12})$alkyl.

2. The compound of claim 1, wherein each of the aryl and heteroaromatic substituents in, (c) and (d) are nitro, amino, cyano, hydroxy, epoxy, vinyl, allyl, hydroxyethoxy, methoxyethoxy, hydroxyethoxyethoxy, methoxyethoxyethoxy fluoro, chloro, bromo, or iodo, $(C_1-C_{12})$alkyl, $(C_1-C_{12})$alkoxy, $(C_1-C_{12})$alkylaryl, aryl, aryloxy, aryl $(C_1-C_{12})$alkyl, aryl$(C_1-C_{12})$alkoxy, $(C_1-C_{12})$alkoxyaryl, halo$(C_1-C_{12})$alkyl, haloaryl, cyclo$(C_3-C_{12})$alkyl, cyclo$(C_1-C_{12})$alkoxy, aryloxyaryl, aryloxy$(C_1-C_{12})$alkyl, aryloxy$(C_1-C_{12})$alkoxy, acryloxy, methacryloxy, or
a heterocyclic nitrogen-containing substituent.

3. The compound of claim 1, wherein X is carbon or nitrogen, $R_1$ and $R_2$ are each independently hydrogen, nitro, cyano, allyl, fluoro, chloro, bromo, trichloromethyl, pyrrolidino, piperidino, morpholino, phenyl, benzyl, a linear or branched $(C_1-C_6)$alkyl, $(C_1-C_6)$alkoxy, or a —OCOR or —COOR group wherein R is hydrogen, $(C_1-C_6)$alkyl, or $(C_3-C_6)$cycloalkyl;
n is an integer from 0 to 2; and
A and A' are each independently:
(a) a linear or branched $(C_1-C_6)$alkyl, $(C_3-C_6)$ cycloalkyl, aryl$(C_1-C_4)$alkyl heteroaryl$(C_1-C_4)$ alkyl, or $(C_1-C_6)$alkoxy$(C_1-C_6)$alkyl;
(b) unsubstituted or mono- or di-substituted aryl, such as phenyl or naphthyl; and
(c) unsubstituted or mono-substituted heteroaromatic groups.

4. The compound of claim 3, wherein each of the aryl and heteroaromatic substituents in (b) and (c) are independently nitro, amino, cyano, hydroxy, epoxy, hydroxyethoxy, methoxyethoxy, hydroxyethoxyethoxy, methoxyethoxyethoxy, fluoro, chloro, bromo, or iodo, vinyl, allyl, phenyl, $(C_1-C_6)$alkyl, $(C_1-C_6)$alkoxy, cyclo$(C_3-C_6)$ alkyl, cyclo$(C_1-C_6)$alkoxy, $(C_1-C_6)$)alkylamino, di$(C_1-C_6)$ alkylamino, diarylamino, phenylacetylenyl, phenylvinyl, or a heterocyclic nitrogen-containing substituent.

5. The compound of claim 4, wherein the heterocyclic nitrogen-containing substituent is N$(C_1-C_6)$alkylpiperazino, N-aryl-piperizino, aziridino, indolino, pyrrolidino, pyrrolino, piperidino, $(C_1-C_4)$alkylpiperidino, di$(C_1-C_4)$ alkylpiperidino, 4-piperidinopiperidino, morpholino, 2,6-di$(C_1-C_4)$alkylmorpholino, thiomorpholino, thioazolidino, tetrahydroquinolino, pyrryl, or a —N$(R_1)R_2$, CON$(R_1)R_2$ wherein $R_1$ and $R_2$ are each independently hydrogen, $(C_1-C_6)$alkyl, $(C_3-C_6)$cycloalkyl, phenyl, or —COR, —OCOR or —COOR wherein R is hydrogen, $(C_1-C_6)$alkyl, $(C_3-C_6)$cycloalkyl, or phenyl.

6. The compound of claim 1, wherein X is carbon or nitrogen; $R_1$, $R_2$ are each independently hydrogen, nitro, cyano, fluoro, chloro, bromo, pyrrolidino, piperidino, morpholino, phenyl, benzyl, $(C_1-C_4)$alkyl, or $(C_1-C_4)$ alkoxy;
n is an integer from 0 to 2; and
A and A' are each independently a linear or branched $(C_1-C_4)$alkyl, $(C_3-C_6)$cycloalkyl, unsubstituted or mono-, or di-substituted phenyl and unsubstituted or mono-substituted heteroaromatic groups.

7. The compound of claim 6, wherein the mono- or disubstituted phenyl group is substituted in the met; par; or both positions with a substituent selected from the group consisting of nitro, amino, acyl, cyano, methoxy, ethoxy, methoxyethoxy, fluoro, chloro, vinyl, allyl, methoxycarbonyl, ethoxycarbonyl, $(C_1-C_4)$alkyl, di$(C_1-C_4)$ alkylamino, piperazino, piperidino, arylperidino, morpholino, pyrrolidino, aziridino, acryloxy, methacryloxy, phenylacetylenyl, and phenylvinyl and the heteroaromatic groups are selected from the group consisting of furyl, thienyl, and pyrryl subsituted with a substituent selected from the group consisting of $(C_1-C_4)$alkyl, and phenyl.

8. A compound selected from the group consisting of:
2,2-diphenyl-phenanthro (9,10)-2H-[1,4]-oxazine,
2-(p-methoxyphenyl)-2-phenyl-phenanthro (9,10)-2H-[1,4]-oxazin,
2-(p-fluorophenyl)-2-(p-methoxyphenyl)-phenanthro (9,10)-2H-[1,4]-oxazine,
2,2-Bis(p-methoxyphenyl)-phenanthro (9,10)-2H-[1,4]-oxazine,
2-p-methoxyphenyl)-2-(p-morpholinophenyl)-phenanthro (9,10)-2H-[1,4]-oxazine,
2-(p-methoxyphenyl)-2-(p-piperidinophenyl)-phenanthro (9,10)-2H-[1,4]-oxazine,
2-methyl-2-phenyl-phenanthro (9,10)-2H-[1,4]-oxazine,
2-cyclopropyl-2-phenyl-phenanthro (9,10)-2H-[1,4]-oxazine,
2,2-diphenyl-6,11-dinitro-phenanthro (9,10)-2H-[1,4]-oxazine,
2-(p-methoxyphenyl)-2-phenyl-6,11-dinitro-phenanthro (9,10)-2H-[1,4]-oxazine,
2,2-Bis(p-methoxyphenyl)-6,11-dinitro-phenanthro (9,10)-2H-[1,4]-oxazine,
2,2-diphenyl-phenanthrolino (5,6)-2H-[1,4]-oxazine,
2-(p-methoxyphenyl)-2-phenyl-(phenanthrolino (5,6)-2H-[1,4]-oxazine; and
2,2-Bis(p-methoxyphenyl-phenanthrolino (5,6)-2H-[1,4]-oxazine.

9. A method for producing an oxazine compound comprising the steps of:

mixing reactive effective amounts of a substituted acrylic acid, an azide source, a mild organic base, 1,8-diazabicyclo[5,4,0]undec-7-ene, a quinone and a catalytic amount of triaryl arsen oxide, in an organic solvent heating the mixture for a time sufficient to complete the reaction to form the oxazine compound.

10. The method of claim 9, wherein the azide source is diphenylphosphoryl azide, or trimethylsilylazide, the base is triethylamine, diisopropyl amine, diisopropyl ethylamine, pyridine, piperidine, morpholine, or N-alkyl morpholine, the quinone is phenanthrene (9,10)-dione or phenanthroline (5,6)-dione, and the triaryl arsen oxide is triphenyl arsen oxide.

* * * * *

UNITED STATES PATENT AND TRADEMARK OFFICE
CERTIFICATE OF CORRECTION

PATENT NO. : 6,720,420 B2
DATED : April 13, 2004
INVENTOR(S) : Zhao et al.

It is certified that error appears in the above-identified patent and that said Letters Patent is hereby corrected as shown below:

Column 14,
Line 27, "$(C_1-C_4)$alkyl" should read -- $(C_1-C_6)$alkyl --

Column 15,
Line 8, "$(C_3-C_{12}$alkyl" should read -- $(C_3-C_{12})$alkyl --

Column 16,
Line 30, "in the met; par; or" should read -- in the meta; para; or --
Line 44, "4]-oxazin," should read -- 4]-oxazine, --
Line 49, "2-p-methoxyphenyl" should read -- 2-(p-methoxyphenyl --

Signed and Sealed this

Sixth Day of July, 2004

JON W. DUDAS
*Acting Director of the United States Patent and Trademark Office*